United States Patent [19]

Shene

[11] Patent Number: 4,938,210
[45] Date of Patent: Jul. 3, 1990

[54] INHALATION CHAMBER IN VENTILATOR CIRCUIT

[75] Inventor: William R. Shene, Plattsburgh, N.Y.

[73] Assignee: Trudell Medical, London, Canada

[21] Appl. No.: 342,809

[22] Filed: Apr. 25, 1989

[51] Int. Cl.⁵ .................. A61M 11/08; A61M 16/08; A61M 16/16
[52] U.S. Cl. .................. 128/203.12; 128/200.23; 128/205.23; 128/204.18; 128/912
[58] Field of Search .................. 128/200.14, 200.23, 128/200.24, 202.22, 202.27, 203.12, 203.21, 204.18, 205.23, 911, 912

[56] References Cited

U.S. PATENT DOCUMENTS

| | | | |
|---|---|---|---|
| 2,631,757 | 3/1953 | Alexander | 128/200.23 |
| 2,890,697 | 6/1959 | Van Sickle | 128/200.23 |
| 3,910,222 | 10/1975 | Metivier | 128/202.22 |
| 4,550,726 | 11/1985 | McEwen | 128/202.22 |
| 4,805,609 | 2/1989 | Roberts et al. | 128/202.27 |

FOREIGN PATENT DOCUMENTS

| | | | |
|---|---|---|---|
| 0275105 | 7/1988 | European Pat. Off. | 128/200.24 |
| 1488249 | 10/1977 | United Kingdom | 128/200.14 |

OTHER PUBLICATIONS

"Portable Equip. for Gen. Anaesthesia...", *The Lancet*, 12/9/1961, p. 1290.

Primary Examiner—Edgar S. Burr
Assistant Examiner—Kimberly L. Asher
Attorney, Agent, or Firm—Robert M. Wolters

[57] ABSTRACT

A ventilator breathing circuit is provided with an inline axially extensible inhalation chamber. Telescoping conduits are disposed within the chamber and normally are in fluid communication. The chamber comprises a pleated outer shell so that it may be axially extended upon separation of the telescoping conduits. A receptacle is provided opening into the chamber for receiving a metered dose inhalation medication cannister. In addition, an air leakage path is provided from the chamber which is designed to be covered manually during use, but which will provide an audible signal if the chamber is left in extended position and unattended.

15 Claims, 1 Drawing Sheet

U.S. Patent
Jul. 3, 1990
4,938,210
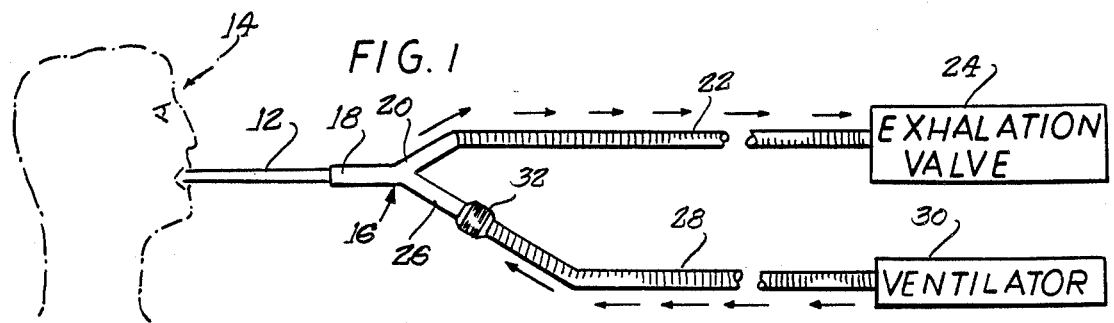
FIG. 1
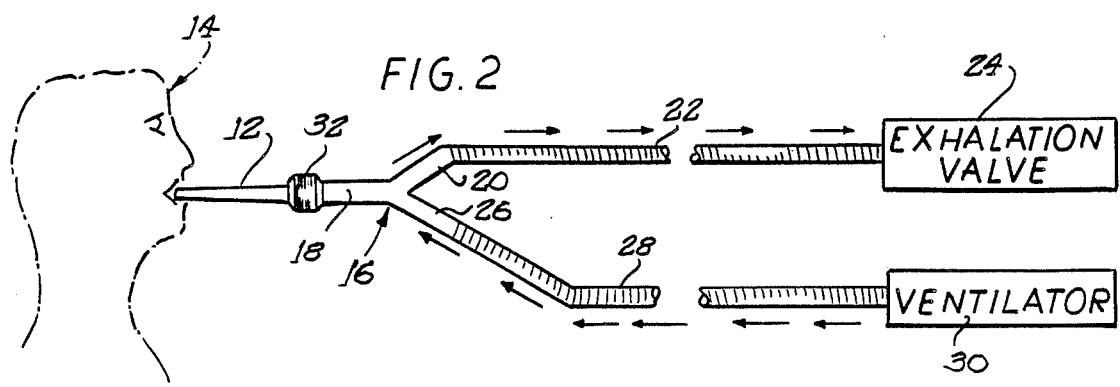
FIG. 2
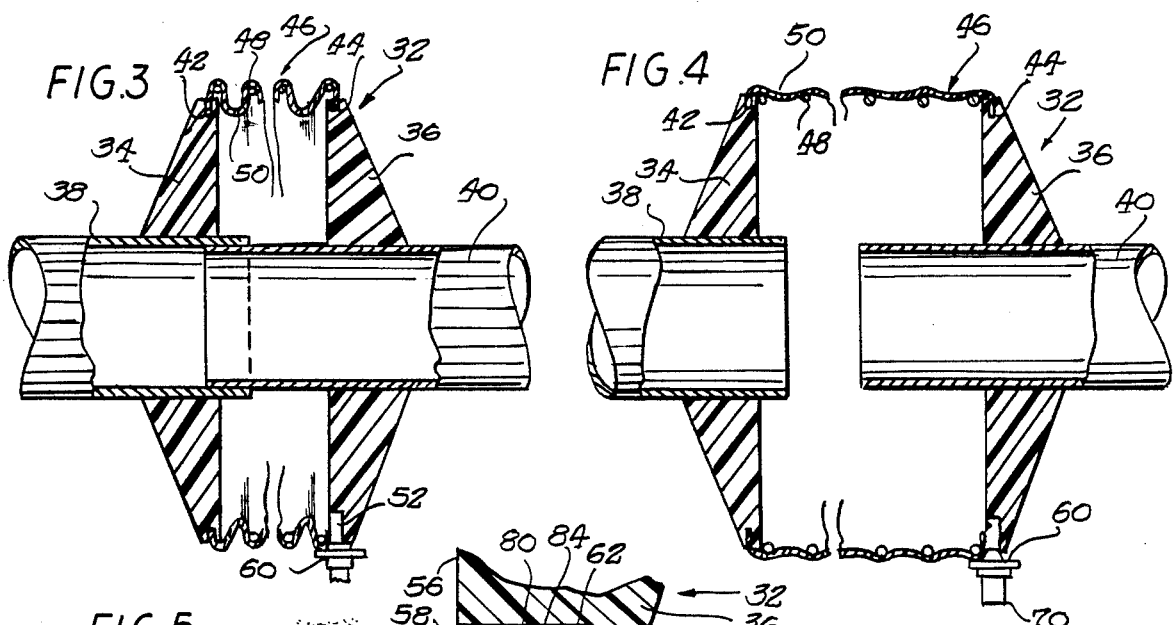
FIG. 3
FIG. 4
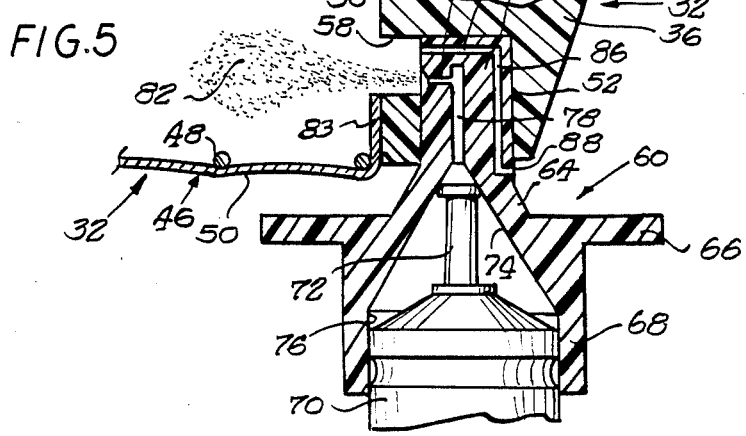
FIG. 5

INHALATION CHAMBER IN VENTILATOR CIRCUIT

BACKGROUND OF THE INVENTION

Often when a patient has trouble breathing by himself, it is necessary to use a ventilator. This may incorporate mechanical or forced inhalation, and generally also includes an endotracheal tube extending through the patient's mouth and into his trachea. A wye connector connects the endotracheal tube with the ventilator and also with an exhalation valve.

Some patients under ventilatory support or coming out of anesthesia tend to have bronchospasms and need a bronchodilator. In the past, it has generally been necessary to open the ventilator circuit in order to introduce a bronchodilator. This takes time, and frequently there is a crisis condition where very little time is available for administrating a bronchodilator. It is known that an elongated cylindrical chamber between a metered dose inhaler or injector materially improves misting of the medication, see for example Nowacki and Brisson U.S. Pat. No. 4,470,412. Herefore it has been necessary to open the ventilating circuit in order to utilize such a device.

OBJECTS AND SUMMARY OF THE PRESENT INVENTION

It is an object of the present invention permanently to incorporate a medication inhalation chamber in a ventilator breathing circuit.

More particularly, it is an object of the present invention permanently to incorporate a medication inhalation chamber in a ventilator breathing circuit which does not add any inspiratory volume to the ventilator breathing circuit except during dispensation of medication.

In carrying out the foregoing and other objects I provide an axially collapsable and expandable medication inhalation chamber coaxial with and disposed exteriorly of tubing in the inhalation portion of a ventilator breathing circuit. A telescoping, locking and separable connection is provided in the tubing within the chamber. This tubing is normally in telescoped position and the medication inhalation chamber is in a passive or inactive state. It does not add any volume whatsoever to the ventilator breathing circuit. It provides no opportunity for gas leaks or for collection of condensed moisture. When it is medically desirable for the patient to inhale medication, then the tubing is unlocked and is axially separated, and the medication chamber is axially extended into operative position. Medication then is injected into the geometrical center of the chamber for optimum suspension of particles and subsequent inhalation by the patient.

The axially extendible chamber preferably comprises a spiral wire with a relatively thin plastic material on the outside thereof, generally similar to that commonly used in flexible ductwork for clothes dryers. However, it is contemplated that other accordian pleating could be used, or even a slip connection between telescoping cylinders.

The medication inhalation chamber can be connected in the breathing circuit in either of two places. It can be in the inspiratory limb just upstream of the wye piece, or it can be between the wye piece and the patient. Generally, it is desired that the device should be positioned as close to the patient as possible.

The circuit between the wye piece and the patient is known as "dead space". This dead space is an important factor in ventilation, since a portion of exhaled carbon dioxide always remains in this "dead space" and is rebreathed by the patient in the next breath. If the medication inhalation chamber is located in this position, then in the collapsed or passive position, it adds very little to the air space. Additional volume in the inspiratory limb is not a serious consideration.

THE DRAWINGS

The present invention will best be understood with reference to the following description when taken in connection with the accompanying drawings wherein:

FIG. 1 comprises a somewhat schematic side view of apparatus incorporating the present invention;

FIG. 2 is a view similar to FIG. 1 showing the medication inhalation chamber in a different position;

FIG. 3 is an axial sectional view of the medication inhalation chamber in collapsed position;

FIG. 4 is a view similar to FIG. 3 with the chamber in extended position; and

FIG. 5 is an axial sectional view on an enlarged scale showing the structure for accommodating the metered dose injection canister.

DETAILED DESCRIPTION OF THE PRESENT INVENTION

Turning now in greater particularity to the figures of the drawings, and first to FIG. 1, there will be seen an exemplification of a ventilator circuit incorporating an inhalation chamber in accordance with the present invention. FIG. 1 is schematic in nature, and there is shown an endotracheal tube 12 intended to be received in the mouth and trachea of a patient 14. The endotracheal tube 12 is connected to a wye piece 16 having a leg 18 and a first branch arm 20 connected through a flexible tubing 22 to an exhalation valve. Exhaled air travels through the arm 20 and tubing 22 an indicated by the arrows, namely from left to right in FIG. 1. The wye piece 16 includes a second branch arm 26 which is connected by way of an inhalation chamber 32 to tubing 28 connected to a ventilator 30. Flow in this tubing 28, chamber 32, and branch arm 26 is from right to left as indicated by the adjacent arrows in FIG. 1. As will be appreciated, the ventilator may supply oxygen and air mixed under pressure in appropriate quantities to force breathing.

FIG. 2 illustrates a second embodiment of the invention. The parts are the same, as shown in FIG. 1, and like numerals are utilized to identify the same parts. The distinction in this case is that the inhalation chamber 32 is disposed between the endotracheal tube 12 and the leg 18 of the wye piece 16.

There are advantages and disadvantages with the two different locations as illustrated in FIGS. 1 and 2, but in general the inhalation chamber should be positioned as close to the patient as possible.

The medication inhalation chamber 32 is shown in greater detail in FIGS. 3 and 4. It includes a pair of molded plastic end pieces 34 and 36 which are mounted on and secured to rigid tubular conduits or pipes 38 and 40, respectively. The conduits or pipes are received in the wye piece leg 27 and the tubing 28, or in the endotracheal tube 12 and wye piece leg 18, respectively in accordance with FIGS. 1 and 2. The end pieces are substantially frustoconical in nature, and are adhesively or otherwise suitably secured to the conduits or pipes 38 and 40. The end pieces are respectively provided with circumferential kerfs 42 and 44, and the end edges of axially collapsable and extendable tubular material 46 are adhesively or otherwise suitably secured therein. Although various types of accordian pleated material could be used to form the tubular material 46, the preferred form of the invention incorporates a spiral spring wire 48 having fairly thin, plastic material 50 stretched thereover. This is similar to the material commonly used for venting clothes dryers. In the passive state of the inhalation chamber 32 the ends of the pipes 38 and 40 are telescoped and locked toghether, as shown in FIG. 3, and the chamber 32 has no effect whatsoever on the ventilator breathing circuit. However, when it is intended to use the medication inhaling facility of the chamber, then the two pipes 38 and 40 or the end pieces 34 and 36, are grasped and twisted slightly to unlock while pulling axially apart, to separate the pipes and extend the chamber 32 as shown in FIG. 4.

The end piece 36 is provided with a radial bore 52 extending in from the pheriphery thereof, and connecting with the inner face 56 of the end piece 36 by a passagway 58 extending from the bore 52 to the space within the inhalation chamber 32. A molded plastic receptacle 60 is inserted into the bore 52, and may be permanently secured in place as by an adhesive, or it may be frictionally held in place for removal when not needed, or when replacement should become necessary.

The receptacle 60 includes an extending nose piece 62 which fits within the bore 52. The nose piece tapers outwardly at 64 exterior of the end piece 36 and a peripheral flange 66 extends radially outwardly for gripping by the fingers. The receptacle continues as a cylinder 68 extending axially beyond the flange 66.

The cylinder 68 is hollow for receipt of the discharge end of a metered dose inhaler cartridge 70. The tubular valve 72 of the cartridge extends to a position near the apex of a conically tapered extension 74 of the hollow interior 76 of the cylinder 68. The apex of the tapered portion 74 has an axially extending bore 78 extending up substantially into alignment with the opening or channel 58 and a lateral extension 80 thereof extends outwardly of the extending nose 62 of the receptacle 60. Thus, when the nurse or other medication dispenser grasps the flange 66 and pushes in on the cartridge 70 a metered dose of medication will be discharged into the bore or channel 78, and will pass out of the lateral bore 80 as a mist as shown at 82 located at the geometric center of the expanded chamber 32. The mist is enhanced by spreading out within the chamber 32. It will be noted that the end or edge of the flexible plastic material 50 is secured at 83 against the inner face 56 of the end piece 36 outwardly of the opening 38, such as by a suitable adhesive. The nose piece will be seen additionally to include a bore 84 extending laterally to the right from the edge of the nose piece opening to the bore or opening 58, and then axially out at 86 down toward the flange 66, and outwardly of the periphery of the end piece 36. The bore 86 then continues at 88 to the right and outwardly of the receptacle 60.

If the patient utilizing the ventilator breathing circuit shown should require a bronchodialator such as epinephrine or other inhalable medication, then the nurse, physician or other attendant simply grasps the end pieces 34 and 36, or the pipes 38 and 40 and relatively twists them while pulling them apart. This extends the chamber to its active position as shown in FIG. 4. The attendant then or simultaneously covers the bore 86 with a finger, while gripping the flange 56 on the end thereof opposite to the cannister 70 while depressing the cannister with the thumb or palm of the hand. This causes the mist 82 to be injected into the geometrical center of chamber 32 for complete misting, and for being carried into the patient's lungs by the air/oxygen mixture from the ventilator. Additional doses of medication may be injected as necessary.

When the patient has received sufficient inhalation medication, then the ends of the pipes 38 and 40 are simply telescoped back together and locked, returning the outer portion 46 to the position shown in FIG. 3. If the nurse or other attendant should be distracted without first collapsing the inhalation chamber 32, then the finger will be removed from the exit bore 86, and this will result in air passing through the bore 84 and 88 and this will cause whistle or hiss that will be audibly discernable to call attention to the fact that the chamber has been left in extended position. In addition, such a leak will cause ventilator alarms to activate if employed. The chamber should not be left in extended position when it is not being used for medication inhalation, since it will act as a water trap. The internal walls of the chamber will become wet and will drastically reduce aerosal delivery when next used, as the drug particles simply stick to anything wet.

The expandable and collapsable inhalation chamber in the ventilator circuit is quite inexpensive in construction, and is simply discarded along with the disposable breathing circuit when it is no longer needed by the patient.

The inhalation chamber as disclosed herein provides minimum dead space when collapsed. However, when it is extended or expanded for use as in FIG. 4, the chamber volume is substantially equal to that in the device in U.S. Pat. No. 4,470,412 mentioned earlier. The present medication inhaler can be left connected in the circuit indefinitely, as it does nothing when in the collapsed position. Substantially no additional dead space is produced, certainly not enough to be of any consequence. The device will accommodate a standard MDI (measured dose inhaler) canister or cartridge to provide the desired aerosol drug. If the present inhalation chamber is left in the extended or expanded position of FIG. 4 and unattended, then there will be air leakage through the bore 84, 86, 88 which will provide an audible sound that will alert the attendant to collapse the chamber to the inactive or passive condition of FIG. 3.

Certain of the parts are shown somewhat out of proportion for convenience of illustration. For example, the chamber would in extended position be longer that its diameter, and this is indicated by the break as shown in FIG. 4. The proportions of the length and diameter would be substantially the same as shown in U.S. Pat. No. 4,470,412, mentioned heretofore. Furthermore, the receptacle 60 does not have to be a separate piece, but could be molded integral with the end piece 36.

In any event, the specific examples of the invention as herein show and described are for illustrative purposes only. Various changes in structure will no doubt occur to those skilled in the art and will be understood as forming a part of the present invention insofar as they fall within the spirit and scope of the appended claims.

The invention is claimed as follows:

1. The combination comprising a ventilator breathing circuit including an inhalation conduit, including a pair of axially separable conduit means of substantially equal predetermined diameter normally in closed fluid communication with one another, an inline axially extensible medication inhalation chamber having a pair of end pieces respectively connected to said conduit means and further having axially extensible substantially cylindrical means of greater diameter than said predetermined diameter interconnecting said end pieces and when axially extended forming with said end pieces a substantially cylindrical medication inhalation chamber, and receptacle means opening into said chamber and adapted to receive a metered dose inhaler cannister for misting aerosol medication into said medication inhalation chamber.

2. The combination set forth in claim 1 wherein said receptacle means is disposed in one of said end pieces.

3. The combination set forth in claim 1 wherein said substantially cylindrical means is substantially accordian pleated.

4. The combination set forth in claim 3 wherein said substantially cylindrical means comprises a spiral support and overlying sheet material.

5. The combination as set forth in claim 4 wherein said sheet material comprises plastic material.

6. The combination set forth in claim 3 wherein said spiral support comprises a wire helix.

7. The combination as set forth in claim 6 wherein the overlying sheet material comprises plastic.

8. The combination as set forth in claim 1 wherein the axially separable conduit means comprises a pair of telescoping tubular members.

9. The combination as set forth in claim 8 wherein the substantially cylindrical means comprises substantially accordian pleated means.

10. The combination as set forth in claim 9 wherein said accordian pleated means comprises a helical wire and plastic sheet material thereover.

11. The combination as set forth in claim 1 and further including means providing an air leakage path from said chamber adapted to be manually covered when in use, and providing an audible warning if said chamber is left unattended in axially extended condition.

12. The combination as set forth in claim 11 wherein the means providing the air leakage path comprises said receptacle.

13. The combination as set forth in claim 12 wherein said substantially cylindrical means comprises a helical wire support and plastic sheet material thereover.

14. The combination as set forth in claim 12 wherein the axially separable conduit means comprises telescoping tubular members.

15. The combination as set forth in claim 14 wherein said substantially cylindrical means comprises a helical supporting wire and overlying plastic sheet material.

* * * * *